United States Patent
Wan et al.

(10) Patent No.: US 12,030,854 B2
(45) Date of Patent: Jul. 9, 2024

(54) METHOD FOR PRODUCING DICHLORO ADDITION PRODUCT OF ALIPHATIC OLEFIN BY PHOTOCATALYSIS UNDER VISIBLE LIGHT

(71) Applicant: SOOCHOW UNIVERSITY, Suzhou (CN)

(72) Inventors: Xiaobing Wan, Suzhou (CN); Pengcheng Lian, Suzhou (CN); Wenhao Long, Suzhou (CN); Jingjing Li, Suzhou (CN); Yonggao Zheng, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 671 days.

(21) Appl. No.: 17/296,542

(22) PCT Filed: Jul. 21, 2020

(86) PCT No.: PCT/CN2020/103302
§ 371 (c)(1),
(2) Date: May 24, 2021

(87) PCT Pub. No.: WO2021/174748
PCT Pub. Date: Sep. 10, 2021

(65) Prior Publication Data
US 2022/0127228 A1    Apr. 28, 2022

(30) Foreign Application Priority Data

Mar. 5, 2020   (CN) .......................... 202010148280.6

(51) Int. Cl.
| | | |
|---|---|---|
| *C07D 209/48* | (2006.01) | |
| *C07B 39/00* | (2006.01) | |
| *C07C 67/287* | (2006.01) | |
| *C07C 201/12* | (2006.01) | |
| *C07C 253/30* | (2006.01) | |
| *C07C 303/40* | (2006.01) | |
| *C07C 315/04* | (2006.01) | |

(52) U.S. Cl.
CPC ............ *C07D 209/48* (2013.01); *C07B 39/00* (2013.01); *C07C 67/287* (2013.01); *C07C 201/12* (2013.01); *C07C 253/30* (2013.01); *C07C 303/40* (2013.01); *C07C 315/04* (2013.01)

(58) Field of Classification Search
None
See application file for complete search history.

(56) References Cited

FOREIGN PATENT DOCUMENTS

| CN | 103304355 A | 9/2013 |
|---|---|---|
| CN | 110753679 A | 2/2020 |
| CN | 111253207 A | 6/2020 |
| CN | 111253254 A | 6/2020 |

OTHER PUBLICATIONS

Misono et al., Regio- and stereoselectivity of substitution of 2-halobutanes by chlorine and stereochemistry of chlorine addition to 2-butenes with copper (II) chloride, Nippon Kagaku Kaishi, No. 12, vol. 1980, pp. 1844-1849 (Dec. 10, 1980).

Tu, "An improved technology for synthesis of 4-methylthiophenol" Guangdong Chemical Engineering, 1998, No. 1, pp. 16 and 25 (Feb. 15, 1998).

*Primary Examiner* — Zinna Northington Davis
(74) *Attorney, Agent, or Firm* — SZDC Law PC

(57) ABSTRACT

The invention provides a method for producing a dichloro addition product of an aliphatic olefin by photocatalysis under visible light. The method includes reacting an aliphatic olefin as a substrate with hydrochloric acid as a chlorine source in an organic solvent under visible light irradiation in the presence of copper chloride with visible light absorption ability as a catalyst, to obtain the dichloro addition product of the aliphatic olefin, wherein the reaction is carried out under an oxygen-containing atmosphere, the aliphatic olefin comprises a carbon-carbon double bond and a C9-C15 aliphatic chain connected to the carbon-carbon double bond by a covalent bond. In the invention, visible light is used to provide the energy and a transition metal chloride with visible light absorption ability is used to undergo light-induced electron transfer from chloride with a reaction substrate, thereby initiating an addition reaction to obtain a dichloro addition product.

9 Claims, No Drawings

METHOD FOR PRODUCING DICHLORO ADDITION PRODUCT OF ALIPHATIC OLEFIN BY PHOTOCATALYSIS UNDER VISIBLE LIGHT

This application is the National Stage Application of PCT/CN2020/103302, filed on Jul. 21, 2020, which claims priority to Chinese Patent Application No. 202010148280.6, filed on Mar. 5, 2020, which is incorporated by reference for all purposes as if fully set forth herein.

FIELD OF THE INVENTION

The present invention relates to the technical field of synthesis of dichloro addition products, and more particularly to a method for producing a dichloro addition product of an aliphatic olefin by photocatalysis under visible light.

DESCRIPTION OF THE RELATED ART

There are more than 2,000 kinds of natural products containing a dichloro structure, and these natural products are often used as chiral catalysts, pharmaceutical intermediates, and organic synthesis intermediates. The introduction of chlorine atoms will significantly change the physical and chemical properties of these compounds, which are often used in the fields of medicine, pesticides, and materials science. Therefore, the synthesis of dichloro-containing compounds is particularly important. Through literature surveys, it is found that the current methods for synthesizing dichloro compounds have some shortcomings, such as harsh reaction conditions, low yield, narrow substrate range, and the need for toxic, harmful and heavy pollution-causing chlorine sources. For example,
  (1) BabakBorhan et al. reported the addition of DCDMH (1,3-dichloro-5,5-dimethylhydantoin) to an olefin by using a chiral catalyst $(DHQD)_2PHAL$, to obtain a dichloro compound. However, expensive catalyst, a large amount of an inorganic salt, and relatively limited reaction substrate are needed. This method focuses on allyl amide compounds and is not suitable for use with ordinary aromatic olefins and aliphatic olefins (see: BabakBorhan; *J. Am. Chem. Soc.* 2017, 139, 2132-2135).
  (2) Rendy Kartika et al. reported the use of potassium peroxomonosulfonate and ammonium chloride to produce chloride cations which are then subjected to addition of chloronium ions to styrene. This process requires a large amount of dangerous inorganic salt oxidant, which incurs both safety hazards and serious environmental pollution (see: Nama Narender, *Synthesis.* 2014, 46, 251-257).
  (3) James B. Hendrickson et al. reported the use of an epoxy compound, triphosgene, and pyridine to generate a chloronium ion-like intermediate to obtain a dichloro compound. The synthesis of the raw material epoxy compound is cumbersome, the substrate is relatively limited, and the reaction conditions are relatively dangerous (see: James B. Hendrickson; *J. Org. Chem.* 2018, 83, 3367-3377).
  (4) Song Lin et al. reported the use of transition metal manganese as a catalyst and magnesium chloride as a chlorine source to generate by means of electrocatalysis and then the chlorine free radicals undergo radical addition to an olefin to produce a dichlorinated product. This system is relatively new. However, dangerous strong oxidant lithium perchlorate is used as an electrolyte, and the reaction system is complicated (See: Song Lin; *J. Am. Chem. Soc.* 2017, 139, 15548-15553).
  (5) CN103304355 A, CN103304367 A, CN103382144 A and CN106831314A disclose the halogenation reaction or halogenation by double-bond addition of alkanes, cycloalkanes, alkyl aromatic hydrocarbons, olefins or olefin derivatives, in which visible light is used to provide the energy required for the reaction, hydrohalic acid or a hydrohalide is used as the halogenating agent, and the substrate is reacted in the presence of a nano-precious metal/semiconductor surface plasma composite as a catalyst to obtain the final product. The catalyst used in the above reaction is a precious metal catalyst, which is expensive. In addition, the semiconductor gap in the photocatalyst needs to be used to transfer the electrons of the halide anion. This process causes a partial loss of the light energy absorbed by the catalyst. In addition, the above reaction system is nano-heterogeneous catalysis, which has the disadvantage of poor repeatability.

In summary, the currently reported methods for synthesizing dichloro compounds have cumbersome reaction processes, require toxic chlorine sources and harsh reaction conditions, and suffer from low yield and simple reaction modes (most of them are thermal reactions). Therefore, it is particularly important to develop a green, mild, efficient, energy-saving, and environmentally friendly visible light-catalyzed chlorination method having abundant sources of raw materials.

SUMMARY OF THE INVENTION

To solve the above technical problems, an object of the present invention is to provide a method for producing a dichloro addition product of an aliphatic olefin by photocatalysis under visible light. In the present invention, visible light is used to provide the energy required for the reaction, and a transition metal chloride with visible light absorption ability is used to undergo light-induced electron transfer with a reaction substrate, thereby initiating an addition reaction to obtain a dichloro addition product. The method of the present invention has mild reaction conditions, simple operations and has wide applicability to a variety of substrates.

To achieve the above purpose, the following technical solutions are adopted in the present invention.

A method for producing a dichloro addition product of an aliphatic olefin by photocatalysis under visible light according to the present invention comprises the following steps:
  reacting an aliphatic olefin as a substrate with hydrochloric acid as a chlorine source in an organic solvent under visible light irradiation in the presence of copper chloride with visible light absorption ability as a catalyst, to obtain a dichloro addition product of the aliphatic olefin where the reaction is carried out under an oxygen-containing atmosphere; the aliphatic olefin comprises a carbon-carbon double bond and a C9-C15 aliphatic chain connected to the carbon-carbon double bond by a covalent bond.

Preferably, the aliphatic olefin is a terminal olefin having a structural formula of

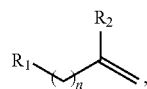

and the structural formula of the dichloro addition product of the aliphatic olefin is

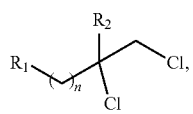

where $R_1$ is selected from hydrogen, substituted or unsubstituted C6-C9 aryl, C6-C9 aryloxy, C1-C4 alkoxy, C6-C9 arylacyloxy or C6-C9 arylsulfonamido;
R2 is selected from hydrogen or C1-C4 alkyl; and
n=1-3.

Preferably, the aryl is selected from phenyl, phenylhydroxyl, phthalimido or naphthyl, where the substituent on substituted aryl is selected from C1-C4 alkyl, C1-C4 alkoxy, C1-C4 alkylsulfonyl, nitro, phenyl, halo, trifluoromethyl, acetoxy, cyano or carboxyl.

Preferably, the arylacyloxy is selected from a phthalimido-containing acyloxy group, a naphthyl-containing acyloxy group or a phenyl ring-containing acyloxy group.

Preferably, the arylsulfonamido is selected from a naphthyl-containing arylsulfonamido group.

Preferably, $R_2$ is selected from hydrogen or methyl.
Preferably, $R_1$ is selected from

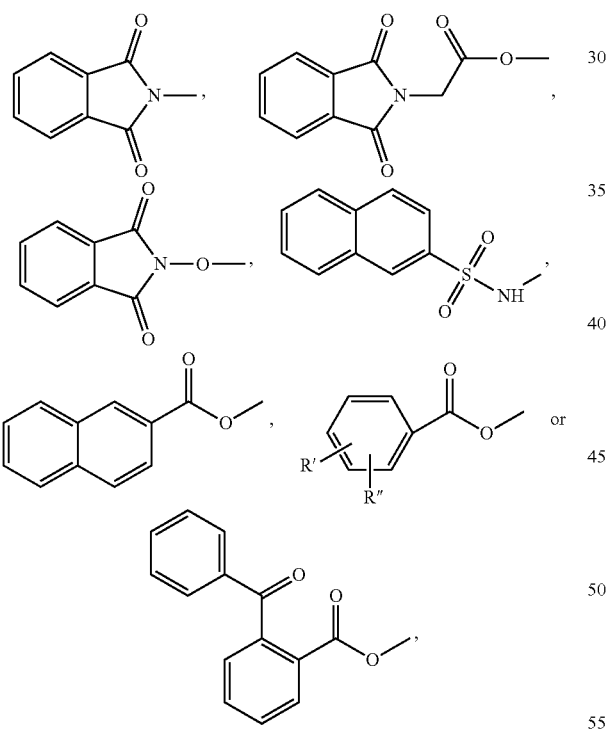

in which R' and R" are independently selected from hydrogen, methyl, methoxy, halo, phenyl, cyano, trifluoromethyl, nitro or

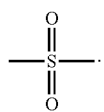

More preferably, the aliphatic olefin has a structural formula selected from:

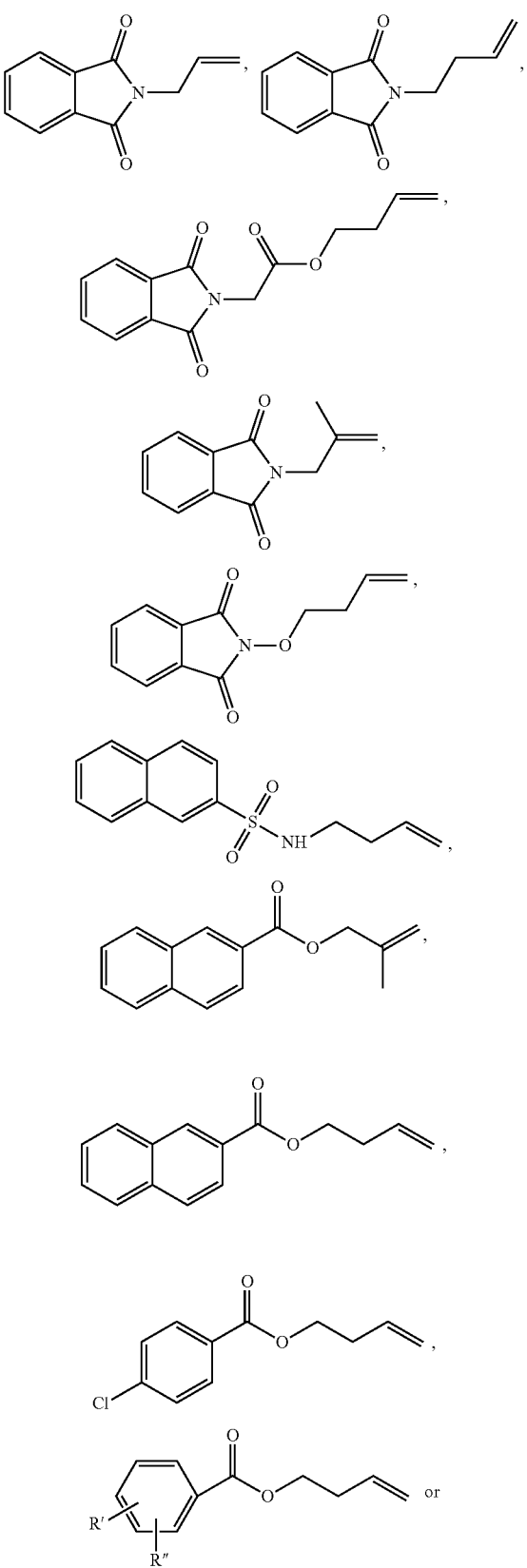

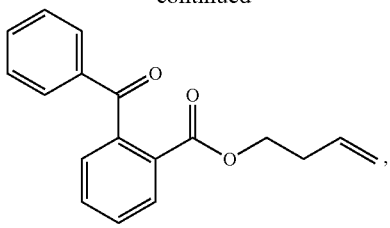

in which R' and R" are independently selected from hydrogen, methyl, methoxy, halo, phenyl, cyano, trifluoromethyl, nitro or

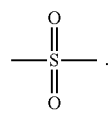

Preferably, the halo is fluoro, chloro, bromo or iodo.

Preferably, the reaction temperature is 23-25° C.; and the reaction time is 36-72 h. More preferably, the reaction time is 72 h.

Preferably, the organic solvent is selected from the group consisting of petroleum ether, 1,2-dichloroethane, 1,1,1-trichloroethane, 1,1,2-trichloroethane, nitromethane, acetonitrile, ethyl acetate, acetone and any combination thereof. Preferably, the organic solvent is acetonitrile.

Preferably, the oxygen-containing atmosphere is pure oxygen or air. More preferably, the oxygen-containing atmosphere is air.

Preferably, the amount of the catalyst is 20% of the molar amount of the aliphatic olefin, and the amount of hydrochloric acid is 2.5 times the molar amount of the aliphatic olefin.

Preferably, the light source of visible light is LED light. The LED light can be white, green or blue; and the power is 18 W-38 W.

Preferably, the light source of visible light is a white LED light with a power of 38 W.

Preferably, after the reaction is complete, the method further comprises the steps of drying the product over anhydrous sodium sulfate, removing the solvent by a rotary evaporator and purification by column chromatography.

The "light" in the photoreaction is a special reagent that can participate in the reaction. A metal complex, an organic dye or a semiconductor able to absorb visible light is used as a photosensitizer, to undergo light-induced electron transfer with the reaction substrate to form a cation free radical or anion free radical of the substrate, thereby triggering the subsequent reaction. Compared with the typical thermochemical reaction, the photochemical reaction has the following characteristics: (1) The thermochemical reaction requires larger activation energy and needs to be heated to a certain temperature before the reaction can occur. In contrast, the photochemical reaction does not require activation energy or requires very low activation energy. Therefore, the photochemical reaction can generally be carried out quickly at room temperature without heating. (2) A complex molecule often contains multiple active groups. In the thermochemical reaction, when one of the groups is reacted, the other groups need to be protected. In the photochemical reaction, a certain group can be excited to react by selecting light of a specific wavelength according to the position of the group in the molecule and the wavelength of light absorbed. 3) In most cases, the products of thermochemical reaction and photochemical reaction are different, so the photochemical reaction can be used to synthesize products that cannot be synthesized by the thermochemical reaction.

In the present invention, a green, environmentally friendly, mild, efficient, and energy-saving visible light-catalyzed strategy is employed to synthesize a dichloro compound. In the present invention, the light source is visible light, and hydrochloric acid, the catalyst, and the organic solvent are all commercial products and can be purchased directly.

The reaction mechanism of the present invention is as follows. The catalyst (copper chloride with visible light absorption ability) absorbs visible light and an LMCT process occurs to generate chlorine free radicals, which then undergo an addition reaction with the aliphatic olefin substrate to obtain a target product. During the process, hydrochloric acid is used as a chlorine source, and copper chloride is regenerated by completing the conversion of the valence of the copper catalyst in an oxygen-containing atmosphere, to complete the recycle of the catalyst.

By means of the above technical solutions, the present invention has the following advantages.

1. In the present invention, a visible light catalysis is employed to prepare a dichloro compound. Compared with the existing technology of synthesizing a dichloride, the present invention has the advantages such as cleanliness, mild reaction conditions, energy saving, cost saving.

2. The method of the present invention does not require pretreatment of the chlorine source, and commercial hydrochloric acid and copper chloride with visible light absorption ability can be directly used in the reaction, thereby avoiding the problem of overly cumbersome operations.

3. In the method of the present invention, an olefin substrate is used as a reaction raw material. Compared with the prior art, the use of an epoxy compound as a reaction raw material is avoided and thus the operation is convenient.

4. In the method of the present invention, copper chloride with visible light absorption ability is used as a catalyst. Compared with the prior art, the use of expensive metals such as iridium, ruthenium, and palladium is avoided, and the light energy utilization efficiency is high.

The above description is only a summary of the technical solutions of the present invention. To make the technical means of the present invention clearer and implementable in accordance with the disclosure of the specification, the preferred embodiments of the present invention will be described in detail.

DETAILED DESCRIPTION OF THE PREFERRED EMBODIMENTS

The present invention will be illustrated in further detail with reference to embodiments. The following embodiments are intended to describe the present invention, instead of limiting the scope of the present invention.

In the present invention, according to the different structures, the substrate olefin can be prepared with a starting material such as a carboxylic acid, or an alcohol, an amine, a phenol.

Example 1

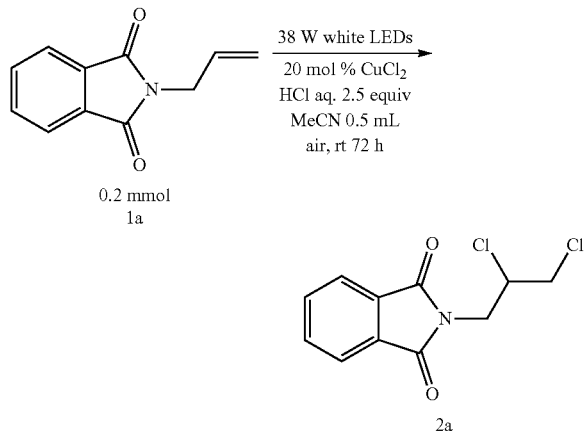

1a (0.2 mmol, 37.4 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution, and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2a (yield 85%). The main test data of the prepared product is shown below. It can be known through analysis that the actually synthesized product is consistent with the theoretical analysis.

$^1$H NMR (400 MHz, CDCl$_3$) δ 7.90-7.88 (m, 2H), 7.78-7.75 (m, 2H), 4.57-4.51 m, 1H), 4.12-4.10 (d, J=6.8 Hz, 2H), 3.87-3.78 (m, 2H). $^{13}$C NMR (100 MHz, CDCl$_3$) δ 167.7, 134.2, 131.6, 123.5, 57.0, 46.2, 41.8; HRMS (ESI-TOF): Anal Calcd. For C$_{11}$H$_9$$^{35}$Cl$^{35}$ClNO$_2$+Na$^+$: 279.9903, Found: 279.9916. Anal Calcd. For C$_{11}$H$_9$$^{35}$Cl$^{37}$ClO$_2$+Na$^+$: 281.9873, 281.9882; IR (neat, cm$^{-1}$): b 3058, 2969, 1706, 1612, 1427, 720.

Example 2

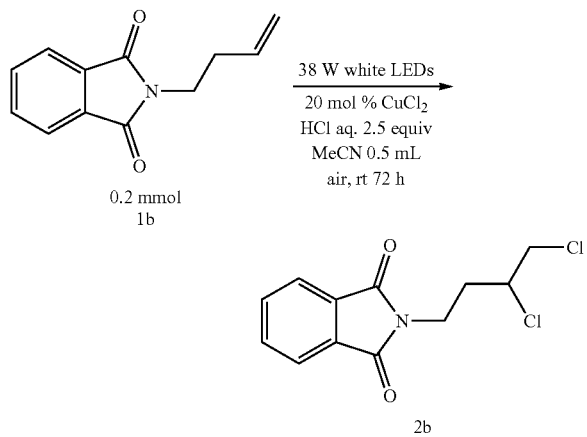

1b (0.2 mmol, 40.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2b (yield 77%). The main test data of the prepared product is shown below. It can be known through analysis that the actually synthesized product is consistent with the theoretical analysis.

$^1$H NMR (400 MHz, CDCl$_3$) δ 7.87-7.85 (m, 2H), 7.75-7.73 (m, 2H), 4.13-4.07 (m, 1H), 3.97-3.87 (m, 2H), 3.86-3.81 (m, 1H), 3.73-3.68 (m, 1H), 2.49-2.41 (m, 1H), 2.15-2.04 (m, 1H). $^{13}$C NMR (100 MHz, CDCl$_3$) δ 168.1, 134.0, 131.9, 123.3, 58.1, 47.8, 35.0, 33.8; HRMS(ESI-TOF): Anal Calcd. For C$_{12}$H$_{11}$$^{35}$Cl$^{35}$ClNO$_2$+Na$^+$: 294.0059, Found: 294.0069. Anal Calcd. For C$_{12}$H$_{11}$$^{35}$Cl$^{37}$ClNO$_2$+Na$^+$: 296.0030, Found: 296.0038. Anal Calcd. For. C$_{12}$H$_{11}$$^{37}$Cl$^{37}$ClNO$_2$+Na$^+$: 298.0000, Found: 297.9995; IR (neat, cm$^{-1}$): b 2996, 2853, 1692, 1609, 1442, 1402, 755.

Example 3

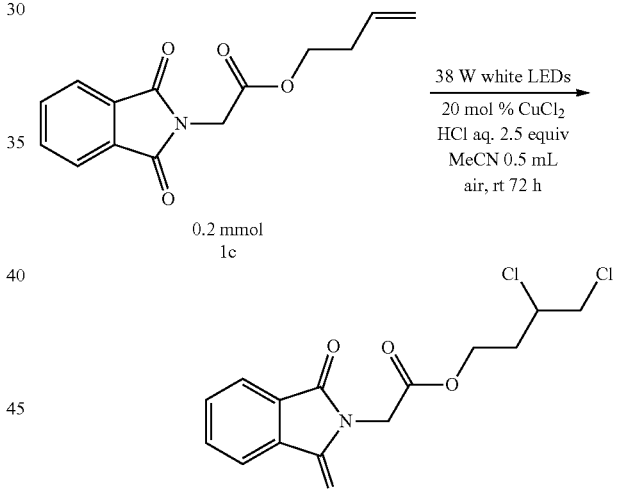

1c (0.2 mmol, 51.8 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2c (yield 63%). The main test data of the prepared product is shown below. It can be known through analysis that the actually synthesized product is consistent with the theoretical analysis.

$^1$H NMR (400 MHz, CDCl$_3$) δ 7.90-7.88 (m, 2H), 7.77-7.75 (m, 2H), 4.47 (s, 2H), 4.44-4.31 (m, 2H), 4.18-4.12 (m,

1H), 3.82-3.78 (m, 1H), 3.70-3.5 m, 1H), 2.43-2.35 (m, 1H), 2.07-1.98 (m, 1H). $^{13}$C NMR (100 MHz, CDCl$_3$) δ 167.3, 167.0, 134.24, 131.8, 123.6, 62.1, 57.0, 48.0, 38.8, 34.0; HRMS (ESI-TOF): Anal Calcd. For $C_{14}H_{13}{}^{35}Cl{}^{35}ClNO_4+Na^+$: 352.0114, $C_{14}H_{13}{}^{35}Cl{}^{37}ClNO_4+Na^+$: 354.0084, $C_{14}H_{13}{}^{37}Cl{}^{37}ClNO_4+Na^+$: 356.0055, Found: 352.0129, 354.0079, 356.0045; IR (neat, cm$^{-1}$): b 2926, 2854, 1754, 1719, 1616, 1469, 1417, 1393, 906, 725.

Example 4

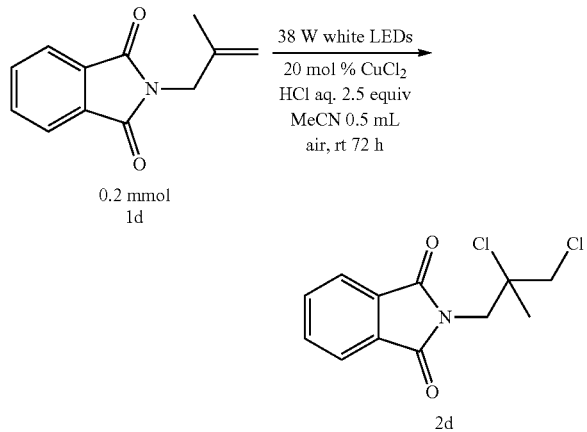

1d (0.2 mmol, 40.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2d (yield 90%). The main test data of the prepared product is shown below. It can be known through analysis that the actually synthesized product is consistent with the theoretical analysis.

$^1$H NMR (400 MHz, CDCl$_3$) δ 7.91-7.88 (m, 2H), 7.78-7.76 (m, 2H), 4.12 (s, 2H), 3.85-3.77 (m, 1H), 1.72 (s, 3H). $^{13}$C NMR (100 MHz, CDCl$_3$) δ 168.1, 134.3, 131.6, 123.6, 69.6, 52.3, 46.1, 26.6; HRMS(ESI-TOF): Anal Calcd. For $C_{12}H_{11}{}^{35}Cl_2NO_2+Na^+$:294.0059, Found: 294.0082. Anal Calcd. For $C_{12}H_{11}{}^{35}Cl{}^{37}ClNO_2+Na^+$: 296.0030, Found: 296.0039. Anal Calcd. For $C_{12}H_{11}{}^{37}Cl_2NO_2+Na^+$: 298.0000, Found: 297.9984; IR (neat, cm$^{-1}$): b 2937, 2860, 1719, 1605, 1394, 905, 723.

Example 5

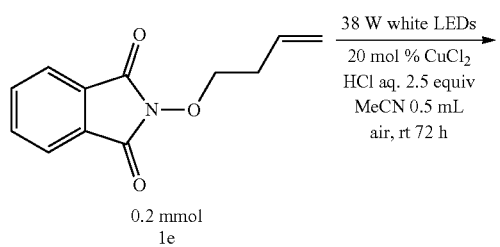

-continued

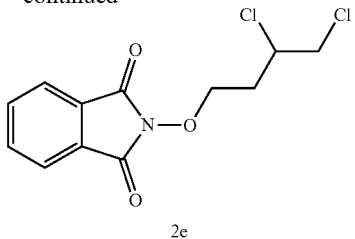

1e (0.2 mmol, 43.4 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2e (yield 68%). The main test data of the prepared product is shown below. It can be known through analysis that the actually synthesized product is consistent with the theoretical analysis.

$^1$H NMR (400 MHz, CDCl$_3$) δ 7.87-7.83 (m, 2H), 7.80-7.75 (m, 2H), 4.66-4.60 (m, 1H), 4.44-4.41 (m, 2H), 3.96-383 (m, 2H), 2.52-2.44 (m, 1H), 2.17-2.09 (m, 1H). $^{13}$C NMR (100 MHz, CDCl$_3$) δ 163.5, 134.6, 128.8, 123.6, 74.7, 57.1, 48.6, 34.1; HRMS (ESI-TOF): Anal Calcd. For $C_{12}H_{11}{}^{35}Cl{}^{35}ClNO_3+Na^+$: 310.0008, Found: 310.0020. Anal Calcd. For. $C_{12}H_{11}{}^{35}Cl{}^{37}ClNO_3+Na^+$:311.9979, Found: 311.9953. Anal Calcd. For $C_{12}H_{11}{}^{37}Cl{}^{37}ClNO_3+Na^+$: 313.9949, Found: 313.9944; IR (neat, cm$^{-1}$): ν 2955, 2924, 1726, 1609, 1467, 1186, 877.698.

Example 6

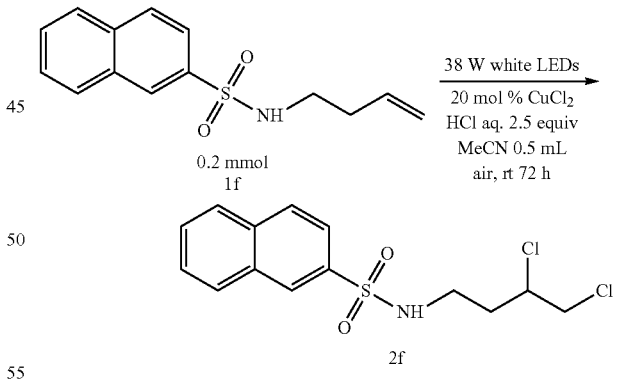

1f (0.2 mmol, 52.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2f (yield 75%). The main test data of the prepared product is shown below. It can be known through analysis that the actually synthesized product is consistent with the theoretical analysis.

$^{1}$H NMR (400 MHz, CDCl$_{3}$) δ 8.46 (d, J=1.4 Hz, 1H), 8.0-7.97 (m, 2H), 7.93-7.91 (d, J=7.9 Hz, 1H), 7.86-7.93 (m, 1H), 7.68-7.60 (m, 2H), 4.92-4.89 (t, J=6.3 Hz, 1H), 4.14-4.11 (m, 1H), 3.76-3.72 (m, 1H), 3.62-3.58 (m, 1H), 3.25-3.19 (m, 2H), 2.30-2.22 (m, 1H), 1.88-1.79 (m, 1H). $^{13}$C NMR (100 MHz, CDCl$_{3}$) δ 136.3, 134.8, 132.1, 129.7, 129.2, 128.9, 128.5, 127.9, 127.6, 122.1, 57.9, 48.0, 40.1, 35.1; HRMS (ESI-TOF): Anal Calcd. For C$_{14}$H$_{15}$$^{35}$Cl$_{2}$NO$_{2}$S+Na$^{+}$: 354.0093, Found: 354.0123. Anal Calcd. For C$_{14}$H$_{15}$$^{35}$Cl$^{37}$ClNO$_{2}$S+Na$^{+}$: 356.0063, Found: 356.0054. Anal Calcd. For C$_{14}$H$_{15}$$^{37}$Cl$_{2}$NO$_{2}$S+Na$^{+}$: 358.0034, Found: 358.0072; IR (neat, cm$^{-1}$): b 3259, 3078, 2956, 2849, 1712, 1587, 1501, 1272.829.

Example 7

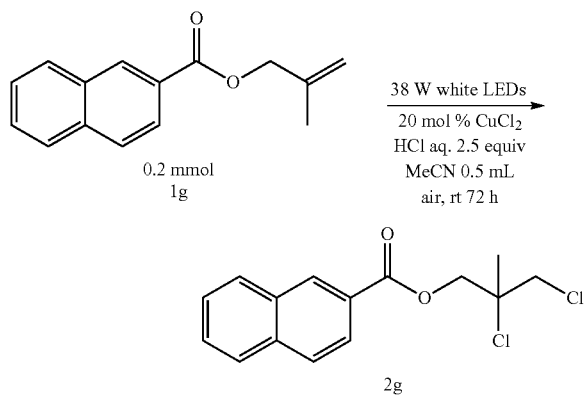 [SMILES: C=C(C)COC(=O)c1ccc2ccccc2c1 ; CC(Cl)(CCl)COC(=O)c1ccc2ccccc2c1]

1g (0.2 mmol, 45.2 mg), CuCl$_{2}$ (0.04 mmol, 5.4 mg), acetonitrile MeCN (0.5 mL), and HCl (0.5 mmol, 41 µL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2g (yield 70%). The main test data of the prepared product is shown below. It can be known through analysis that the actually synthesized product is consistent with the theoretical analysis.

$^{1}$H NMR (400 MHz, CDCl$_{3}$) δ 8.62 (s, 1H), 8.08-8.05 (m, 1H), 7.99-7.97 (d, J=8.0 Hz, 1H), 7.91-7.88 (m, 2H), 7.63-7.54 (m, 2H), 4.62-4.61 (d, J=0.9 Hz, 2H), 4.03-4.00 (d, J=11.5 Hz, 1H), 3.84-3.81 (d, J=11.4 Hz, 1H), 1.78 (s, 3H). $^{13}$C NMR (100 MHz, CDCl$_{3}$) δ 165.8, 135.7, 132.4, 131.3, 129.4, 128.5, 128.4, 127.8, 126.8, 126.6, 125.1, 68.3, 67.6, 49.9, 25.1; HRMS(ESI-TOF): Anal Calcd. For C$_{15}$H$_{14}$$^{35}$Cl$_{2}$O$_{2}$+Na$^{+}$: 319.0263, Found: 319.0285. Anal Calcd. For C$_{15}$H$_{14}$$^{35}$Cl$^{37}$ClO$_{2}$+Na$^{+}$: 321.0234, Found: 321.0214. Anal Calcd. For C$_{15}$H$_{14}$$^{37}$Cl$_{2}$O$_{2}$+Na$^{+}$: 323.0204, Found: 323.0243; IR (neat, cm$^{-1}$): b 3062, 2930, 1719, 1631, 1457, 1279, 1194, 906, 762.

Example 8

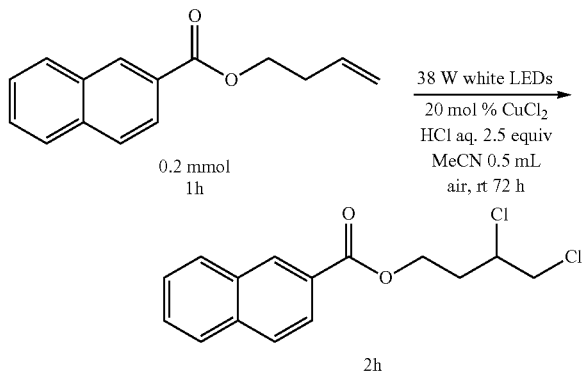

1h (0.2 mmol, 45.2 mg), CuCl$_{2}$ (0.04 mmol, 5.4 mg), acetonitrile MeCN (0.5 mL), and HCl (0.5 mmol, 41 µL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2h (yield 82%). The main test data of the prepared product is shown below. It can be known through analysis that the actually synthesized product is consistent with the theoretical analysis.

$^{1}$H NMR (400 MHz, CDCl$_{3}$) δ 8.60 (m, 1H), 8.05-8.03 (m, 1H), 7.96-7.94 (m, 1H), 7.88-7.86 (m, 2H), 7.61-7.52 (m, 2H), 4.66-4.52 (m, 2H), 4.34-4.28 (m, 1H), 3.89-3.73 (m, 2H), 2.61-2.53 (m, 1H), 2.23-2.14 (m, 1H). $^{13}$C NMR (100 MHz, CDCl$_{3}$) δ 166.4, 135.6, 132.4, 131.1, 129.3, 128.3, 128.2, 127.7, 127.1, 126.7, 125.1, 61.4, 57.5, 48.1, 34.3; HRMS (ESI-TOF): Anal Calcd. For C$_{15}$H$_{14}$$^{35}$Cl$_{2}$O$_{2}$+Na$^{+}$: 319.0263, Found: 319.0291. Anal Calcd. For C$_{15}$H$_{14}$$^{35}$Cl$^{37}$ClO$_{2}$+Na$^{+}$: 321.0234, Found: 321.0233. Anal Calcd. For C$_{15}$H$_{14}$$^{37}$Cl$_{2}$O$_{2}$+Na$^{+}$: 323.0204, Found: 323.0239; IR (neat, cm$^{-1}$): ν 3062, 2963, 1714, 1631, 1467, 1226, 906, 726.

Example 9

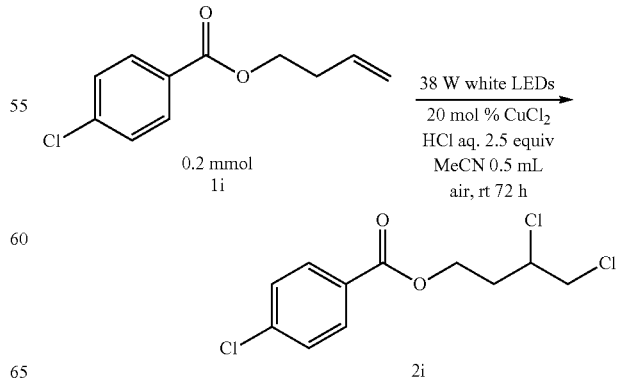

1i (0.2 mmol, 42.0 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2i (yield 81%). The main test data of the prepared product is shown below. It can be known through analysis that the actually synthesized product is consistent with the theoretical analysis.

$^1$H NMR (400 MHz, CDCl$_3$) δ 7.98-7.96 (m, 2H), 7.43-7.41 (m, 2H), 4.60-4.46 (m, 2H), 4.28-4.22 (m, 1H), 3.87-3.71 (m, 2H), 2.57-2.49 (m, 1H), 2.19-2.10 (m, 1H). $^{13}$C NMR (100 MHz, CDCl$_3$) δ 165.4, 139.6, 130.9, 128.8, 128.3, 61.5, 57.4, 48.0, 34.2; HRMS (ESI-TOF): Anal Calcd. For C$_{11}$H$_{11}$$^{35}$Cl$_3$O$_2$+Na$^+$: 302.9717, Found: 302.9729. Anal Calcd. For C$_{11}$H$_{11}$$^{35}$Cl$_2$$^{37}$ClO$_2$+Na$^+$: 304.9687, Found: 304.9677; IR (neat, cm$^{-1}$): b 2963, 2853, 1717, 1594, 1488, 1402, 1267, 849.

Example 10

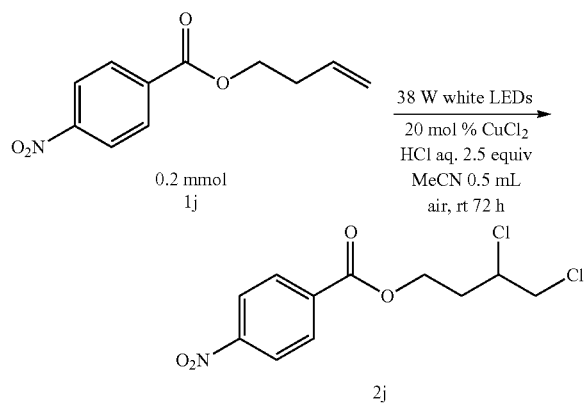

2j 1j (0.2 mmol, 44.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2j (yield 74%). The main test data of the prepared product is shown below. It can be known through analysis that the actually synthesized product is consistent with the theoretical analysis.

$^1$H NMR (400 MHz, CDCl$_3$) δ 8.32-8.29 (m, 2H), 8.23-8.20 (m, 2H), 4.67-4.54 (m, 2H), 4.29-4.22 (m, 1H), 3.90-3.71 (m, 2H), 2.62-2.54 (m, 1H), 2.23-2.14 (m, 1H). $^{13}$C NMR (100 MHz, CDCl$_3$) δ 164.4, 150.6, 135.2, 130.7, 123.6, 62.3, 57.2, 47.9, 34.0; HRMS (ESI-TOF): Anal Calcd. For C$_{11}$H$_{11}$$^{35}$Cl$_2$NO$_4$+Na$^+$: 313.9957, Found: 313.9948. Anal Calcd. For C$_{11}$H$_{11}$$^{35}$Cl$^{37}$ClNO$_4$+Na$^+$: 315.9928; Found: 315.9956; IR (neat, cm$^{-1}$): b 3117, 3057, 2964, 2850, 1719, 1598, 1519, 1439, 1275, 728.

Example 11

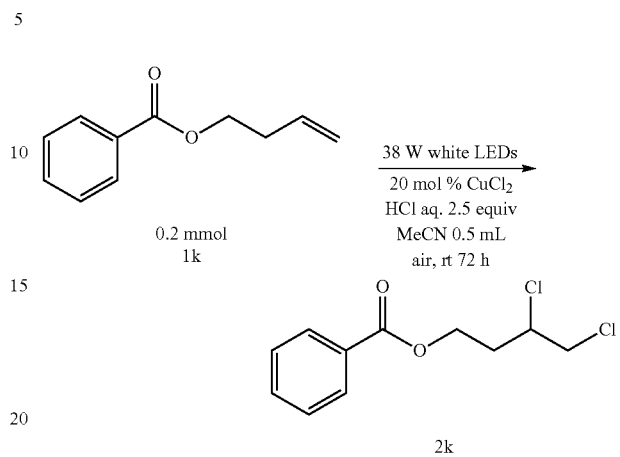

2k 1k (0.2 mmol, 35.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2k (yield 84%). The main test data of the prepared product is shown below. It can be known through analysis that the actually synthesized product is consistent with the theoretical analysis.

$^1$H NMR (400 MHz, CDCl$_3$) δ 8.05-8.03 (m, 2H), 7.60-7.55 (m, 1H), 7.47-7.43 (m, 2H), 4.61-4.46 (m, 2H), 4.31-4.24 (m, 1H), 3.87-3.72 (m, 2H), 2.57-2.49 (m, 1H), 2.19-2.10 (m, 1H). $^{13}$C NMR (100 MHz, CDCl$_3$) δ 166.3, 133.1, 129.8, 129.6, 128.4, 61.3, 57.5, 48.1, 34.2; HRMS (ESI-TOF): Anal Calcd. For C$_{11}$H$_{12}$$^{35}$Cl$_2$O$_2$+Na$^+$: 269.0107, Found: 269.0126. Anal Calcd. For C$_{11}$H$_{12}$$^{35}$Cl$^{37}$ClO$_2$+Na$^+$: 271.0077, Found: 271.0193. Anal Calcd. For C$_{11}$H$_{12}$$^{37}$Cl$_2$O$_2$+Na$^+$: 273.0048, Found: 273.0060; IR (neat, cm$^{-1}$): b 2962, 2926, 1716, 1602, 1452, 1268, 708.

Example 12

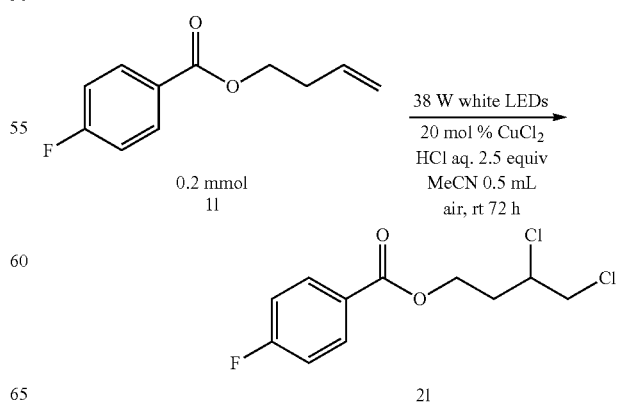

2l 11 (0.2 mmol, 38.8 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 21 (yield 80%). The main test data of the prepared product is shown below. It can be known through analysis that the actually synthesized product is consistent with the theoretical analysis.

$^1$H NMR (400 MHz, CDCl$_3$) δ 8.08-8.03 (m, 2H), 7.15-7.09 (m, 2H), 4.60-4.46 (m, 2H), 4.29-4.23 (m, 1H), 3.88-3.71 (m, 2H), 2.57-2.49 (m, 1H), 2.19-2.10 (m, 1H). $^{13}$C NMR (100 MHz, CDCl$_3$) δ 165.8, 165.3, 132.2, 126.1, 115.6, 61.4, 57.4, 48.0, 34.2; HRMS(ESI-TOF): Anal Calcd. For. C$_{11}$H$_{11}$$^{35}$Cl$_2$FO$_2$+Na$^+$: 287.0012, Found: 287.0014. Anal Calcd. For C$_{11}$H$_{11}$$^{35}$Cl$^{37}$ClFO$_2$+Na$^+$: 288.9983, Found: 288.9964; IR (neat, cm$^{-1}$): b 2963, 2928, 1716, 1603, 1508, 1411, 1387, 1267, 766.

Example 13

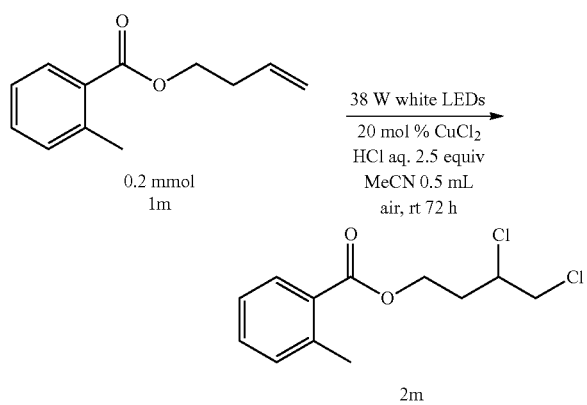

1m (0.2 mmol, 38.0 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2m (yield 71%). The main test data of the prepared product is shown below. It can be known through analysis that the actually synthesized product is consistent with the theoretical analysis.

$^1$H NMR (400 MHz, DMSO) δ 7.87-7.85 (m, 1H), 7.51-7.47 (m, 1H), 7.34-7.30 (m, 2H), 4.53-4.44 (m, 2H), 4.39-4.29 (m, 1H), 4.05-3.97 (m, 2H), 2.53 (s, 3H), 2.42-2.34 (m, 1H), 2.18-2.09 (m, 1H). $^{13}$C NMR (100 MHz, CDCl$_3$) δ 167.2, 140.3, 132.1, 131.8, 130.5, 129.2, 125.8, 61.1, 57.5, 48.1, 34.3, 21.7; HRMS(ESI-TOF): Anal Calcd. For. C$_{12}$H$_{14}$$^{35}$Cl$^{37}$ClO$_2$+Na$^+$: 285.0234, Found: 285.0240.

Anal Calcd. For C$_{12}$H$_{14}$$^{37}$Cl$_2$O$_2$+Na$^+$: 287.0204, Found: 287.0184; IR (neat, cm$^{-1}$): b 2964, 2929, 2855, 1717, 1602, 1576, 1489, 1249, 734.

Example 14

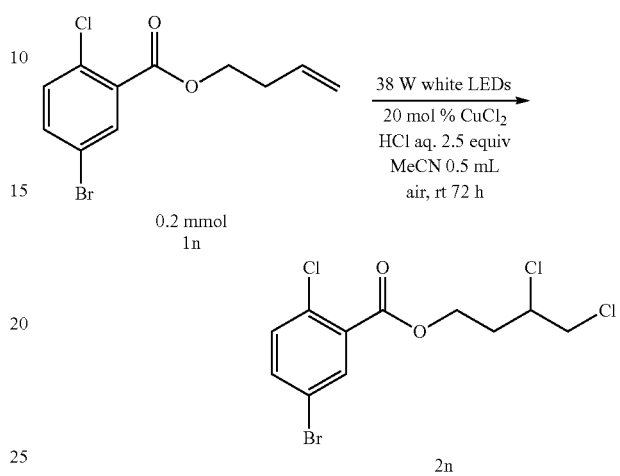

In (0.2 mmol, 57.6 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2n (yield 78%). The main test data of the prepared product is shown below. It can be known through analysis that the actually synthesized product is consistent with the theoretical analysis.

$^1$H NMR (400 MHz, CDCl$_3$) δ 7.96-7.95 (m, 1H), 7.56-7.54 (m, 1H), 7.34-7.32 (m, 1H), 4.63-4.58 (m, 1H), 4.55-4.49 (m, 1H), 4.31-4.25 (m, 1H), 3.88-3.84 (m, 1H), 3.75-3.70 (m, 1H), 2.59-2.51 (m, 1H), 2.17-2.08 (m, 1H). $^{13}$C NMR (100 MHz, CDCl$_3$) δ 164.2, 135.6, 134.2, 132.7, 132.5, 131.3, 120.2, 62.3, 57.2, 48.0, 34.1; HRMS (ESI-TOF): Anal Calcd. For C$_{H}$H$_{10}$$^{79}$Br$^{35}$Cl$_3$O$_2$+Na$^+$: 380.8822, Found: 380.8844. C$_{11}$H$_{10}$$^{79}$Br$^{35}$Cl$_2$$^{37}$ClO$_2$+Na$^+$: 382.8792, Found: 382.8835. C$_{11}$H$_{10}$$^{79}$Br$^{35}$Cl$^{37}$Cl$_2$O$_2$+Na$^+$: 384.8763, Found: 384.8815; IR (neat, cm$^{-1}$): b 2964, 1733, 1600, 1460, 1238, 905, 726.

Example 15

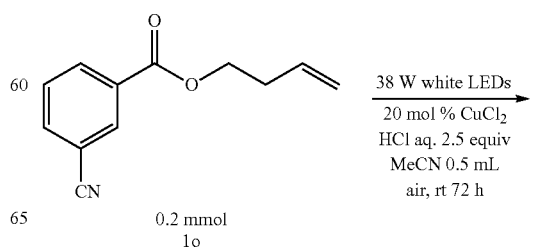

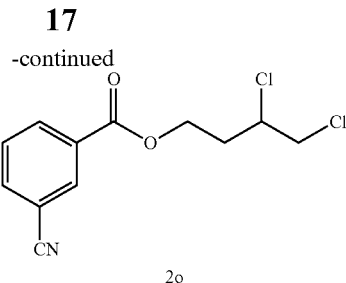

2o 1o (0.2 mmol, 40.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2o (yield 80%). The main test data of the prepared product is shown below. It can be known through analysis that the actually synthesized product is consistent with the theoretical analysis.

$^1$H NMR (400 MHz, CDCl$_3$) δ 8.32-8.27 (m, 2H), 7.88-7.86 (m, 1H), 7.64-7.60 (m, 2H), 4.65-4.52 (m, 2H), 4.31-4.25 (m, 1H), 3.90-3.86 (m, 1H), 3.78-3.74 (m, 1H), 2.60-2.52 (m, 1H), 2.23-2.14 (m, 1H). $^{13}$C NMR (100 MHz, CDCl$_3$) δ 164.2, 136.0, 133.5, 133.1, 131.0, 129.4, 117.7, 112.9, 62.0, 57.2, 47.9, 33.9; HRMS (ESI-TOF): Anal Calcd. For C$_{12}$H$_{11}$$^{35}$Cl$_2$NO$_2$+Na$^+$: 294.0059, Found: 294.0068. Anal Calcd. For C$_{12}$H$_{11}$$^{35}$Cl$^{37}$ClNO$_2$+Na$^+$: 296.0030, Found: 296.0016; IR (neat, cm$^{-1}$): b 3080, 2966, 2234, 1723, 1600, 1433, 1275, 1185, 907, 818, 752.

Example 16

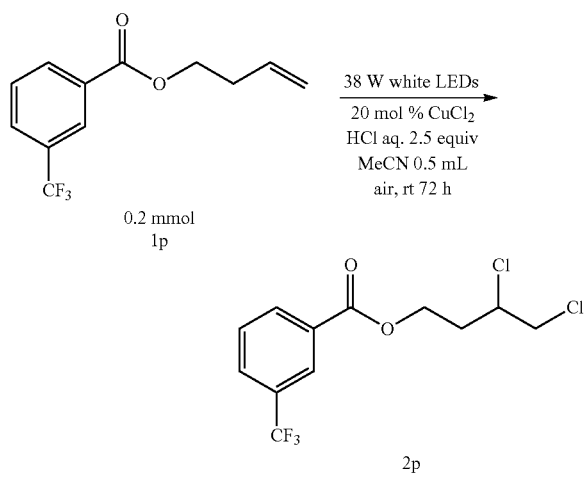

2p 1p (0.2 mmol, 48.8 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2p (yield 66%). The main test data of the prepared product is shown below. It can be known through analysis that the actually synthesized product is consistent with the theoretical analysis.

$^1$H NMR (400 MHz, CDCl$_3$) δ 8.30 (m, 1H), 8.24-8.22 (m, 1H), 7.84-7.82 (m, 1H), 7.62-7.58 (m, 1H), 4.65-4.52 (m, 2H), 4.30-4.23 (m, 1H), 3.89-3.85 (m, 1H), 3.77-3.72 (m, 1H), 2.61-2.52 (m, 1H), 2.23-2.14 (m, 1H). $^{13}$C NMR (100 MHz, CDCl$_3$) δ 165.0, 132.7, 131.1 (q, J=33.0 Hz), 130.7, 129.6 (q, J=3.6 Hz), 129.1, 126.5 (q, J=3.9 Hz), 123.6 (d, J=272.5 Hz), 61.9, 57.3, 47.9, 34.1; HRMS (ESI-TOF): Anal Calcd. For C$_{12}$H$_{11}$$^{35}$Cl$_2$F$_3$O$_2$+Na$^+$: 336.9980, Found: 336.9987; IR (neat, cm$^{-1}$): b 2968, 1724, 1618, 1248, 1126, 907, 756, 693.

Example 17

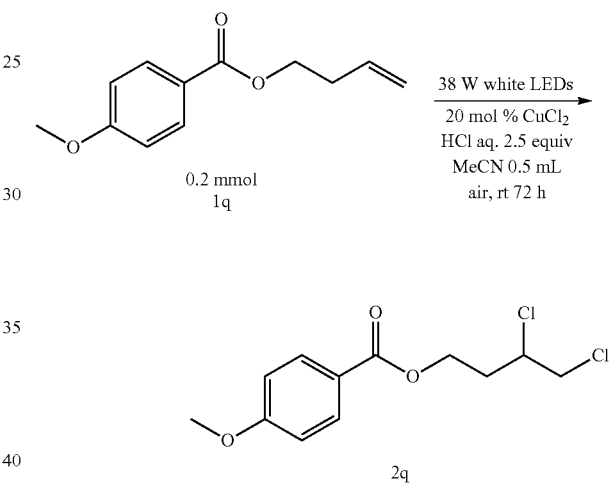

2q 1q (0.2 mmol, 41.2 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2q (yield 74%). The main test data of the prepared product is shown below. It can be known through analysis that the actually synthesized product is consistent with the theoretical analysis.

$^1$H NMR (400 MHz, CDCl$_3$) δ 8.00-7.98 (m, 2H), 6.94-6.91 (m, 2H), 4.57-4.42 (m, 2H), 4.30-4.24 (m, 1H), 3.87-3.83 (m, 4H), 3.76-3.72 (m, 1H), 2.55-2.47 (m, 1H), 2.17-2.09 (m, 1H). $^{13}$C NMR (100 MHz, CDCl$_3$) δ 166.0, 163.5, 131.6, 122.2, 113.6, 60.9, 57.5, 55.4, 48.1, 34.3; HRMS (ESI-TOF): Anal Calcd. For C$_{12}$H$_{14}$$^{35}$Cl$_2$O$_3$+Na$^+$: 299.0212, Found: 299.0224. Anal Calcd. For C$_{12}$H$_{14}$$^{35}$Cl$^{37}$ClO$_3$+Na$^+$: 301.0183, Found: 301.0200; IR (neat, cm$^{-1}$): b 2965, 2841, 1708, 1606, 1512, 1458, 1423, 1254, 1167, 907, 847, 727.

Example 18

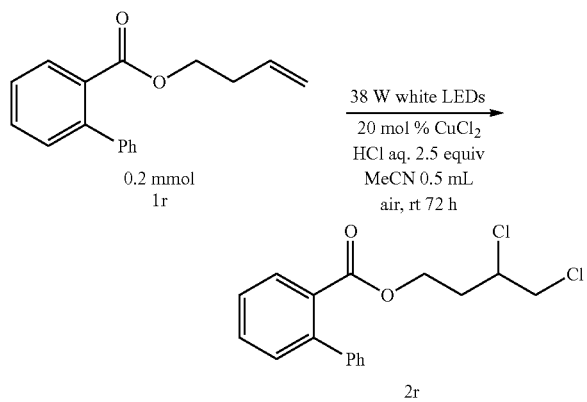

1r (0.2 mmol, 50.4 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2r (yield 65%). The main test data of the prepared product is shown below. It can be known through analysis that the actually synthesized product is consistent with the theoretical analysis.

$^1$H NMR (400 MHz, CDCl$_3$) δ 7.85-7.83 (m, 1H), 7.53-749 (m, 1H), 7.42-7.29 (m, 7H), 4.27-4.21 (m, 1H), 4.18-4.12 (m, 1H), 3.53-3.43 (m, 2H), 3.42-3.35 (m, 1H), 1.94-1.86 (m, 1H), 1.74-1.65 (m, 1H). $^{13}$C NMR (100 MHz, CDCl$_3$) δ 168.5, 142.1, 141.6, 131.3, 130.6, 130.6, 130.0, 128.2, 127.2, 127.1, 61.1, 57.0, 48.3, 33.9; HRMS (ESI-TOF): Anal Calcd. For C$_{17}$H$_{16}$$^{35}$Cl$_2$O$_2$+Na$^+$:345.0420, Found: 345.0403. Anal Calcd. For C$_{17}$H$_{16}$$^{35}$Cl$^{37}$ClO$_2$+Na$^+$: 347.0390, Found: 347.0357. C$_{17}$H$_{16}$$^{37}$Cl$_2$O$_2$+Na$^+$: 349.0361, Found: 349.0322; IR (neat, cm$^{-1}$): b 3063, 2963, 1716, 1598, 1489, 1242, 1048, 907, 700.

Example 19

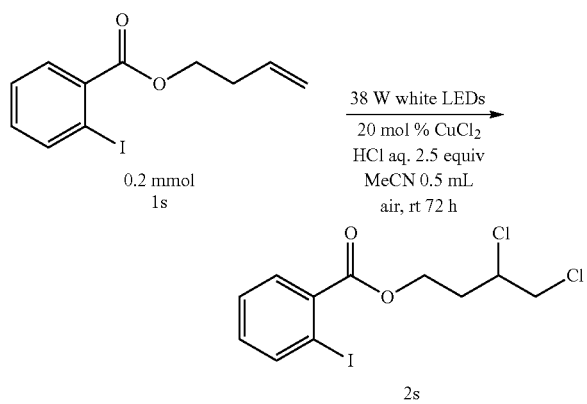

1s (0.2 mmol, 60.4 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2s (yield 57%). The main test data of the prepared product is shown below. It can be known through analysis that the actually synthesized product is consistent with the theoretical analysis.

$^1$H NMR (400 MHz, CDCl$_3$) δ 8.00-7.98 (m, 1H), 7.80-7.77 (m, 1H), 7.43-7.39 (m, 1H), 7.18-7.14 (m, 1H), 4.63-4.57 (m, 1H), 4.51-4.47 (m, 1H), 4.36-4.30 (m, 1H), 3.87-3.83 (m, 1H), 3.76-3.71 (m, 1H), 2.59-2.51 (m, 1H), 2.17-2.08 (m, 1H). $^{13}$C NMR (100 MHz, CDCl$_3$) δ 166.2, 141.2, 134.9, 132.7, 130.9, 127.9, 93.9, 62.0, 57.4, 48.1, 34.1; HRMS(ESI-TOF): Anal Calcd. For C$_{11}$H$_{11}$$^{35}$Cl$_2$IO$_2$+Na$^+$: 394.9073, Found: 394.9082. Anal Calcd. For C$_{11}$H$_{11}$$^{35}$Cl$^{37}$ClIO$_2$+Na$^+$: 396.9043, Found: 396.9060. Anal Calcd. For C$_{11}$H$_{11}$$^{37}$Cl$_2$IO$_2$+Na$^+$: 398.9014, Found: 398.9048; IR (neat, cm$^{-1}$): b 2963, 1725, 1583, 1429, 1247, 907, 729.

Example 20

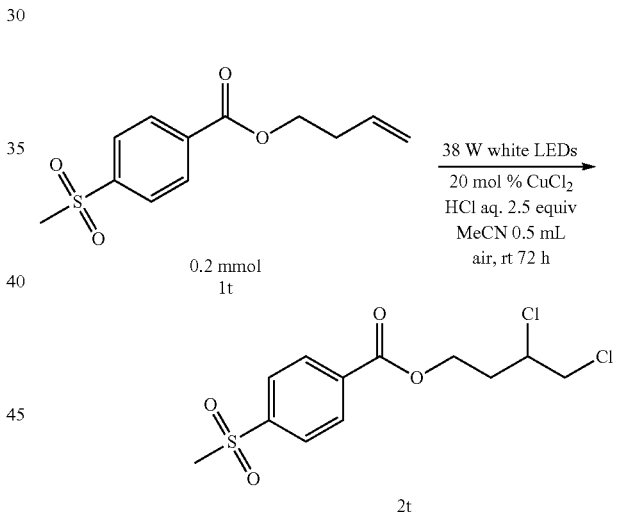

1t (0.2 mmol, 50.8 mg), CuCl$_2$ (0.04 mmol, 5.4 mg), acetonitrile MeCN (0.5 mL), and HCl (0.5 mmol, 41 μL) were added to a test tube. Then the system was irradiated for 72 h with a 38 W white LED light with stirring in the air at room temperature. The reaction system was quenched with a saturated sodium sulfite solution and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2t (yield 61%). The main test data of the prepared product is shown below. It can be known through analysis that the actually synthesized product is consistent with the theoretical analysis.

$^1$H NMR (400 MHz, CDCl$_3$) δ 8.24-8.22 (m, 1H), 8.05-8.03 (m, 1H), 4.66-4.53 (m, 2H), 4.32-4.26 (m, 1H), 3.90-3.86 (m, 1H), 3.79-3.74 (m, 1H), 3.11 (s, 3H), 2.57-2.52 (m,

1H), 2.24-2.15 (m, 1H). $^{13}$C NMR (100 MHz, CDCl$_3$) δ 164.5, 144.3, 134.4, 130.4, 127.4, 62.0, 57.2, 47.9, 44.1, 33.9; HRMS (ESI-TOF): Anal Calcd. For C$_{12}$H$_{14}$$^{35}$Cl$_2$O$_4$S+ Na$^+$: 346.9882, Found: 346.9879. Anal Calcd. For C$_{12}$H$_{14}$$^{35}$Cl$^{37}$ClO$_4$S$_2$+Na$^+$: 348.9853, Found: 348.9814, C$_{12}$H$_{14}$$^{37}$Cl$_2$O$_4$S+Na$^+$: 350.9823, Found: 350.9812; IR (neat, cm$^{-1}$): b 2967, 1725, 1600, 1401, 1271, 906, 724.

Example 21

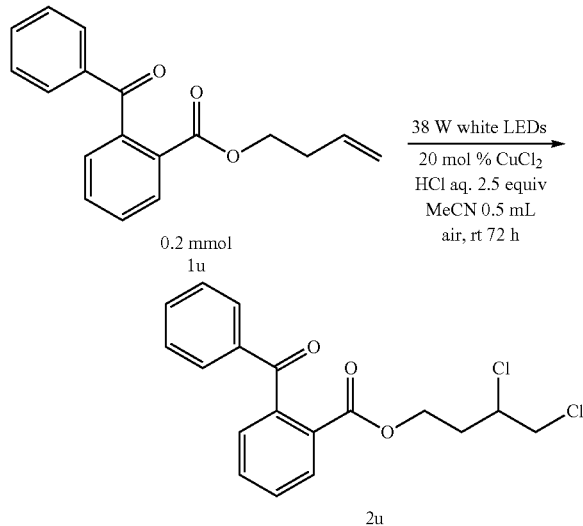

1u (0.2 mmol, 56.0 mg), CuCl$_2$ (0.04 mmol, 5.4 mg), acetonitrile MeCN (0.5 mL), and HCl (0.5 mmol, 41 µL) were added to a test tube. Then the system was irradiated for 72 h with a 38 W white LED light with stirring in the air at room temperature. The reaction system was quenched with a saturated sodium sulfite solution, and extracted 3 times with ethyl acetate. The organic layers were combined and dried over anhydrous sodium sulfate. The solvent was removed by a rotary evaporator, and the residue was adsorbed on silica gel, and purified by simple column chromatography to obtain the product 2u (yield 73%). The main test data of the prepared product is shown below. It can be known through analysis that the actually synthesized product is consistent with the theoretical analysis.

$^1$H NMR (400 MHz, CDCl$_3$) δ 8.08-8.06 (m, 1H), 7.79-7.76 (m, 2H), 7.66-7.62 (m, 1H), 7.60-7.55 (m, 2H), 7.47-7.43 (m, 2H), 7.39-7.37 (m, 1H), 4.31-4.17 (m, 2H), 3.92-3.86 (m, 1H), 3.65-3.61 (m, 1H), 3.57-3.52 (m, 1H), 2.15-2.07 (m, 1H), 1.86-1.78 (m, 1H). $^{13}$C NMR (100 MHz, CDCl$_3$) δ 196.6, 165.6, 141.4, 136.7, 133.3, 132.4, 130.2, 129.6, 129.4, 128.7, 128.5, 127.5, 61.8, 57.1, 48.2, 33.8; HRMS (ESI-TOF): Anal Calcd. For. C$_{18}$H$_{16}$$^{35}$Cl$_2$O$_3$+Na$^+$: 373.0369, Found: 373.0335. Anal Calcd. For C$_{18}$H$_{16}$$^{35}$Cl$^{37}$ClO$_3$+Na$^+$: 375.0339, Found: 375.0316. Anal Calcd. For C$_{18}$H$_{16}$$^{37}$Cl$_2$O$_3$+Na$^+$: 377.0310, Found: 377.0309; IR (neat, cm$^{-1}$): b 3065, 2964, 1719, 1617, 1597, 1275, 908, 767.

In the above examples of the present invention, the white LED light can also be replaced with visible light sources of other colors.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for producing a dichloro addition product of an aliphatic olefin by photocatalysis under visible light, comprising steps of:
   reacting an aliphatic olefin as a substrate with hydrochloric acid as a chlorine source in an organic solvent under visible light irradiation in the presence of copper chloride with visible light absorption ability as a catalyst, to obtain the dichloro addition product of the aliphatic olefin, wherein the reaction is carried out under an oxygen-containing atmosphere; the aliphatic olefin comprises a carbon-carbon double bond and a C9-C15 aliphatic chain connected to the carbon-carbon double bond by a covalent bond.

2. The method according to claim 1, wherein the aliphatic olefin has a structural formula of

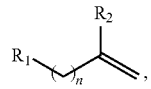

and the dichloro addition product of the aliphatic olefin has a structural formula of

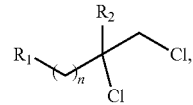

in which R$_1$ is selected from hydrogen, substituted or unsubstituted C7-C13 aryl, C6-C12 aryloxy, C1-C4 alkoxy, C6-C12 arylacyloxy or C6-C12 arylsulfonamido;
R$_2$ is selected from hydrogen or C1-C4 alkyl; and n=1-3.

3. The method according to claim 2, wherein the aryl is selected from phenyl, phenylhydroxyl, phthalimido or naphthyl, where the substituent on the substituted aryl is selected from C1-C4 alkyl, C1-C4 alkoxy, C1-C4 alkylsulfonyl, nitro, phenyl, halo, trifluoromethyl, acetoxy, cyano or carboxyl.

4. The method according to claim 2, wherein the arylacyloxy is selected from a phthalimido-containing acyloxy group, a naphthyl-containing acyloxy group or a phenyl ring-containing acyloxy group; and the arylsulfonamido is selected from a naphthyl-containing arylsulfonamido group.

5. The method according to claim 2, wherein R$_2$ is selected from hydrogen or methyl.

6. The method according to claim 1, wherein the reaction temperature is 23-25° C.; and the reaction time is 36-72 h.

7. The method according to claim 1, wherein the organic solvent is selected from the group consisting of petroleum ether, 1,2-dichloroethane, 1,1,1-trichloroethane, 1,1,2-trichloroethane, nitromethane, acetonitrile, ethyl acetate, acetone and any combination thereof.

8. The method according to claim 1, wherein the oxygen containing atmosphere is pure oxygen or air.

9. The method according to claim 1, wherein the amount of the catalyst is 20% of the molar amount of the aliphatic olefin, and the amount of hydrochloric acid is 2.5 times the molar amount of the aliphatic olefin.

* * * * *